(12) United States Patent
McHugh et al.

(10) Patent No.: US 9,986,905 B2
(45) Date of Patent: Jun. 5, 2018

(54) PREDICTING RETINAL DEGENERATION BASED ON THREE-DIMENSIONAL MODELING OF OXYGEN CONCENTRATION

(71) Applicant: The Schepens Eye Research Institute, Inc., Boston, MA (US)

(72) Inventors: Kevin McHugh, Allston, MA (US); Magali Saint-Geniez, Somerville, MA (US); Leo Kim, Boston, MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 24 days.

(21) Appl. No.: 14/786,952

(22) PCT Filed: Apr. 23, 2014

(86) PCT No.: PCT/US2014/035181
§ 371 (c)(1),
(2) Date: Oct. 23, 2015

(87) PCT Pub. No.: WO2014/176359
PCT Pub. Date: Oct. 30, 2014

(65) Prior Publication Data
US 2016/0100752 A1    Apr. 14, 2016

Related U.S. Application Data

(60) Provisional application No. 61/815,665, filed on Apr. 24, 2013.

(51) Int. Cl.
*A61B 3/14* (2006.01)
*A61B 3/00* (2006.01)
(Continued)

(52) U.S. Cl.
CPC ............ *A61B 3/0025* (2013.01); *A61B 3/102* (2013.01); *A61B 3/1005* (2013.01); *A61B 3/12* (2013.01);
(Continued)

(58) Field of Classification Search
CPC ....... A61B 5/1455; A61B 5/7275; A61B 3/12; A61B 3/1005; A61B 3/102; A61B 3/0025;
(Continued)

(56) References Cited

U.S. PATENT DOCUMENTS

2008/0255457 A1* 10/2008 Khoobehi .......... A61B 5/14555
600/476
2009/0053816 A1* 2/2009 Tezel .................... G01N 33/723
436/67

(Continued)

*Primary Examiner* — Mustak Choudhury
(74) *Attorney, Agent, or Firm* — Mintz Levin Cohn Ferris Glovsky and Popeo, P.C.

(57) ABSTRACT

In some example implementations, there is provided a method for predicting retinal degeneration in multiple eye diseases. The method may include receiving three-dimensional data representative of a plurality of layers of a retina of a subject under test; determining, from the received data, oxygen concentration at one or more of the plurality of layers; detecting, based on the determined oxygen concentration, a region of at least one a high oxygen concentration in the retina or a low oxygen concentration in the retina; and comparing the detected region to reference data to determine whether the retina including the detected region suffers from or will suffer from at least one of a retinal disease or a degeneration of the retina. Related apparatus are also disclosed.

21 Claims, 13 Drawing Sheets

(51) Int. Cl.
  *A61B 5/1455*  (2006.01)
  *A61B 3/12*  (2006.01)
  *A61B 3/10*  (2006.01)
  *A61B 5/00*  (2006.01)

(52) U.S. Cl.
  CPC .......... *A61B 5/1455* (2013.01); *A61B 5/7275* (2013.01); *A61B 5/0066* (2013.01)

(58) Field of Classification Search
  CPC .... A61B 5/14555; A61B 3/10; G01N 33/723; G02B 27/28; G01J 3/02; G01J 3/0208; G01J 3/2823; G01J 3/36; G01J 3/0256
  USPC .......... 351/205, 206, 246, 619; 436/66, 67; 424/172.1; 435/4, 40.52; 514/2.4, 7.7; 600/407; 604/22, 323, 476
  See application file for complete search history.

(56) References Cited

U.S. PATENT DOCUMENTS

| | | | |
|---|---|---|---|
| 2009/0225277 A1* | 9/2009 | Gil ..................... | A61B 5/14555 351/206 |
| 2010/0085537 A1* | 4/2010 | Ramella-Roman | A61B 5/14555 351/205 |
| 2010/0191081 A1* | 7/2010 | Shahidi .............. | A61B 5/14555 600/323 |

* cited by examiner

Bottom

PREDICTING RETINAL DEGENERATION BASED ON THREE-DIMENSIONAL MODELING OF OXYGEN CONCENTRATION

CROSS-REFERENCE TO RELATED APPLICATION

This application is a national-phase entry of Patent Cooperation Treaty Application No. PCT/US2014/035181, entitled "Predicting Retinal Degeneration Based On Three-Dimensional Modeling Of Oxygen Concentration," which has an international filing date of Apr. 23, 2014, and claims the benefit of U.S. Provisional Patent Application Ser. No. 61/815,665, filed Apr. 24, 2013, and entitled "Predicting Retinal Degeneration Based on Three-Dimensional Modeling of Oxygen Concentration," which is incorporated by reference herein in its entirety.

STATEMENT OF GOVERNMENT SUPPORT

This invention was made with government support under grant number 1DP20D006649 awarded by NIH. The government has certain rights to this invention.

TECHNICAL FIELD

This disclosure relates generally to predicting retinal degeneration.

BACKGROUND

Although age-related macular degeneration (AMD) is the leading cause of blindness in the developed world, the techniques for diagnosing and treating eye disease are decidedly lacking. The main indicator used to diagnose pre-symptomatic AMD is the presence of drusen as viewed using fundus photography. Drusen are heterogeneous deposits of oxidized lipids and proteins that form in or on the sub-retinal extracellular matrix sheet termed Bruch's membrane (BrM). BrM is located between the highly metabolic photoreceptors of the outer retina and its main vascular supply, the choriocapillaris, which delivers approximately 90% of the metabolites required by photoreceptors via diffusion. However, when drusen are present in BrM, the distance these metabolites must travel can drastically increase, resulting in a flattening of the concentration gradient and reduction in metabolite delivery. Though small or sparse drusen are recognized as a normal part of aging and not associated with disease progression, large and/or numerous drusen can be considered signs of early AMD. Other hallmarks of AMD include thickening of BrM, decreased BrM hydrolytic conductivity, and vascular dropout, all of which may further contribute to AMD pathology due to inadequate metabolite delivery.

Because oxygen is well-known to be the limiting metabolite in the outer retina, several groups have proposed oxygen deficiency as a key player in multiple degenerative retinal diseases including AMD. Photoreceptors of the outer retina consume oxygen via aerobic respiration to efficiently produce the energy required to maintain dark current for phototransduction. The theory of hypoxia-induced retinal degeneration underlying vision loss is supported by a growing amount of in vitro, in vivo, ex vivo, and clinical evidence.

Numerous studies have demonstrated the importance of oxygen regulation in maintaining retinal cell homeostasis as both hypoxia and hyperoxia are capable of inducing apoptosis. In vivo studies using a variety of animals including rats, cats, and non-human primates have shown that oxygen concentration approaches zero near the layer of photoreceptor inner segments even under healthy conditions. Because oxygen concentration at the inner segment is so tightly-regulated, disease-related morphological changes that are frequently as large as 30% of the retina's total thickness may disrupt this balance of supply and consumption. These changes may be especially critical in the macula, an area where a thinner and more porous BrM has evolved to combat the lack of retinal vasculature and high density of the more metabolically-costly cone photoreceptors.

Clinically, oxygen supplementation has been shown to decrease photoreceptor death in patients with retinal detachment. This therapy aims to counteract the drop in oxygen delivery associated with a pathological increase in diffusion distance by raising the peak dissolved oxygen concentration. Others have shown that photoreceptor degeneration is (approximately 16-fold) more highly correlated with drusen height than with drusen width. This evidence is again congruent with the idea that photoreceptor degeneration may be a result of insufficient metabolite transport due to increased diffusion distance while simultaneously calling into question the validity of using drusen width as the main criteria for AMD diagnosis. In addition, wet AMD (choroidal neovascularization) is likely the body's attempted healing response to outer retinal hypoxia. When challenged with insufficient oxygen, cells of the retina attempt to increase vascular density and perfusion through a vascular endothelial growth factor (VEGF) dependent pathway. However, excessive VEGF signaling in the eye can cause aberrant vessel growth into the neural retina resulting in edema and rapid visual loss as seen in wet AMD.

SUMMARY

In some example implementations, there is provided a method for predicting retinal degeneration and/or retinal diseases. The method may include receiving three-dimensional data representative of a plurality of layers of a retina of a subject under test; determining, from the received data, oxygen concentration at one or more of the plurality of layers; detecting, based on the determined oxygen concentration, a region of at least one a high oxygen concentration in the retina or a low oxygen concentration in the retina; and comparing the detected region to reference data to determine whether the retina including the detected region suffers from or will suffer from at least one of a retinal disease or a degeneration of the retina.

In some variations, one or more of the features disclosed herein including the following features can optionally be included in any feasible combination. The three-dimensional data may include at least one of an optical coherence tomography (OCT) image of the subject under test or a fundus image of the subject under test. The determining may further include determining the oxygen concentration at, or between, one or more of the following layers: a Bruch's membrane, a retinal pigment epithelium; a photoreceptor inner segment-outer segment junction; an external limiting membrane; a top of the outer nuclear layer; and a top of the outer plexiform layer. The reference model may include a three-dimensional model including oxygen concentration data obtained from one or more patients having the at least one of the retinal disease or the degeneration of the retina. The at least one of the retinal disease or the degeneration of the retina may include at least one of a retinal thinning, an age-related macular degeneration (AMD), a retinal edema, retinal detachment, or a central serous retinopathy. A three-dimensional model may be generated, based on the received three-dimensional data, and this model may be specific to the subject under test and may include the plurality of layers of the retina and the oxygen concentration determined for at least one of the plurality of layers. The detected region may be compared to a high oxygen threshold concentration in the retina or a low oxygen threshold concentration in the retina.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

Figure 1A:
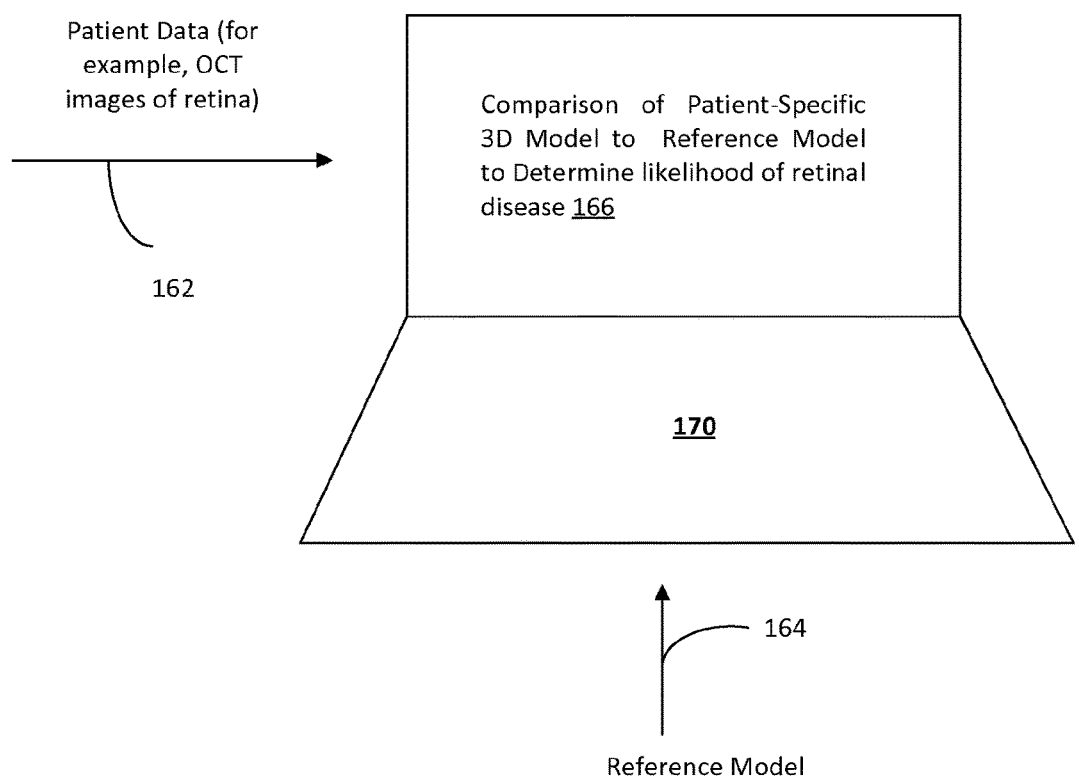
FIG. 1A illustrates an example of a system 160 for predicting retinal degeneration based on three-dimensional oxygen concentration modeling.

Oxygen is known to be a limiting metabolite during normal photoreceptor function. In addition, both hypoxia and hyperoxia have been observed to cause photoreceptor cell death. The normal oxygen transport to photoreceptors may be inhibited by ocular pathologies resulting in increased diffusion distance, reduced supply, or decreased environmental diffusivity. For example, in age-related macular degeneration (AMD), drusen accumulation is observed to increase the distance and potentially decrease the diffusion coefficient between the oxygen supplying choriocapillaris and highly metabolic photoreceptors. As a result, drusen of a critical shape and size may prevent sufficient oxygen transport to the photoreceptor layer leading to decreased photoreceptor function, photoreceptor apoptosis, and visual loss over time. This degenerative process may be the result of decreased energy production and acidification of the local microenvironment which occurs as photoreceptors switch from aerobic to anaerobic respiration under hypoxic conditions. Following this initial degeneration, a secondary stage of photoreceptor degeneration may occur due to hyperoxia at the borders of the void. Oxygen previously used by cells that underwent apoptosis can then contribute to the total amount of oxygen in the adjacent cells' local environment, which may be pathological. Alternately, retinal degeneration above the initial druse may increase its size. Either of these effects may lead to the expansion of the region of photoreceptor degeneration similar to what is observed in geographic atrophy. Drusen-induced hypoxia may be a major contributing factor in the photoreceptor degeneration associated with AMD. Although the number and diameter of drusen observed on fundus images is currently used to diagnose AMD, this metric is frequently a poor predictor of future disease progression and vision loss.

Pathological barriers including, for example drusen and/or the like may interfere with the transport of key metabolites leading to insufficiently nourished cells that perform sub-optimally and eventually die. In the retina, several diseases including age-related macular degeneration (AMD), retinal edema, retinal detachment, and central serous retinopathy increase the distance (and may also decrease environmental metabolite diffusivity) between the vasculature and photoreceptors. As a result, all steady-state metabolite concentrations decrease—particularly at the photoreceptor inner segment—the main consumer of oxygen in the retina.

In some example embodiments, the subject matter disclosed herein relates to predicting maladies of the eye, such as for example retinal degeneration and vision loss related to insufficient transport of oxygen, although other metabolites may be used as well. Moreover, there is provided a patient-specific three-dimensional model of the eye that can be used to assess oxygen concentration in the layers of the retina including the outer retina in order to identify regions of hypoxia and predict future retinal degeneration. Furthermore, there is provided a three-dimensional reference model of the eye, and this reference model may be used to predict retinal degenerations and/or maladies of the eye based on a comparison between the patient-specific three-dimensional model and the three-dimensional reference model.

FIG. 1A depicts a system 100 including a processor, such as a computer 170. The computer 170 may receive patient data 162. For example, the computer 170 may receive patient data obtained from a patient's stack of optical coherence tomography (OCT) images and corresponding fundus images of the eye, although other types of images/data may be received as well. Parameters from the images may be extracted to create a patient-specific three-dimensional (3D) model of the patient's eye and, in particular, to create a morphological representation of the retina including the layers of the retina, the depths of the layers, location of drusen, and other morphological features. This 3D patient-specific model may further include, at each layer of the retina and at a plurality of locations of the retina, parameters relating to actual or simulated values for metabolite supply and/or consumption at and/or between each of the layers. Examples of these parameters include oxygen consumption, oxygen diffusion, oxygen influx, and/or the like. These parameters may be based on simulated values, although actual patient data and/or animal data may be used as well. Next, the steady state oxygen concentration at each of the retina layers of the 3D patient-specific model may be calculated by computer 170. Based on the steady state oxygen concentration throughout the three-dimensional retinal morphology given by the 3D patient-specific model, computer 170 may determine detect regions of interest. These regions may represent areas of hypoxia or regions of hyperoxia, and these regions may be linked to possible current or future retinal degeneration and vision loss. Moreover, these regions may be detected in multiple layers in the 3D patient-specific model of the retina and correlated with the location and shape of drusen and other morphological features and/or metabolic activity in each layer. These regions including their size, shape, position, and location in certain layers may also be used as parameters.

At this point, computer 170 may compare, at 166, the 3D patient-specific model including the above-noted parameters with a 3D reference model, which is further described below. For example, a mathematical or statistical comparison between the patient-specific 3D model and the 3D reference model may provide an indication of the likelihood that the patient's disease will progress. Specifically, the comparison may provide an assessment of the likelihood of having a retinal malady (for example, AMD, retinal edema, central serous retinopathy and/or any other retinal degenerative disease or vision loss due to insufficient transport of oxygen), a speed of progression of the retinal degeneration/disease, and/or a likelihood that the detected regions will worsen or expand and at what rate. This assessment may be provided as an output by processor 170 to enable a care giver to provide an assessment of the eye disease.

The 3D reference model may represent data from one or more patients collected over time to show a progression of retinal degeneration due to hypoxia or hyperoxia (for example, the degree of onset and speed of onset of the retinal degeneration). As such, when the 3D patient-specific model is compared to this 3D reference model, an assessment can be made of the likelihood that the patient associated with the 3D patient-specific model will continue to suffer from retinal degeneration and/or whether the degeneration will develop into a retinal disease as well as the degree, location, and speed of onset of the degeneration/disease.

The 3D reference model may include historical data from one or more actual patients, although simulated data and/or animal data may be used as well. This 3D reference model may have the same or similar form as the 3D patient-specific model with respect to the parameters disclosed herein including the morphology/layers, parameters (for example, metabolite/oxygen consumption and/or the like at various locations/layers), the detected regions, and/or the like. In some example embodiments, the 3D reference model may be generated over time to specifically take into account abnormal oxygenation across the outer retina to allow prediction of vision loss based on this abnormal oxygenation.

Figure 1B:
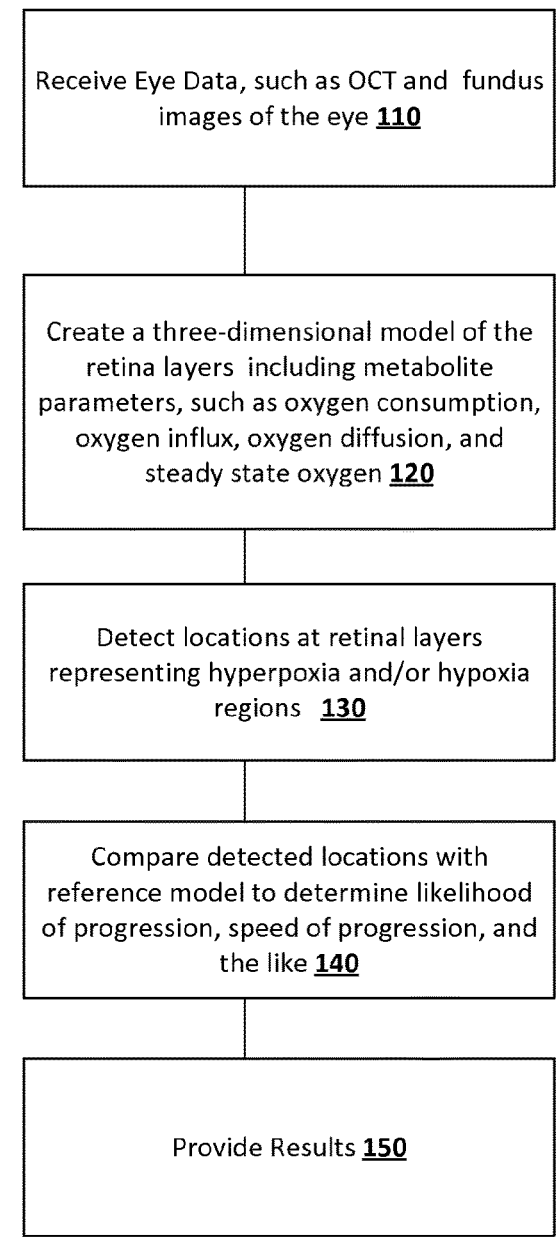
FIG. 1B depicts an example of a process 100 for predicting retinal degeneration based on three-dimensional oxygen concentration modeling.

FIG. 1B depicts a process 100 for predicting retinal degeneration based on three-dimensional modeling of the eye including a metabolite concentration, such as oxygen.

At 110, three-dimensional data, such as OCT and fundus images of the eye, may be received. A processor, such as a computer, may receive OCT image data representative of the morphology of the eye including the retinal layers of a patient under test. For example, a machine may simultaneously capture a group of spatially, sequential optical coherence tomography (OCT) images of a patient's retina, and the machine may then register landmarks and location information for the images to allow processing and combining the images.

Figure 2:
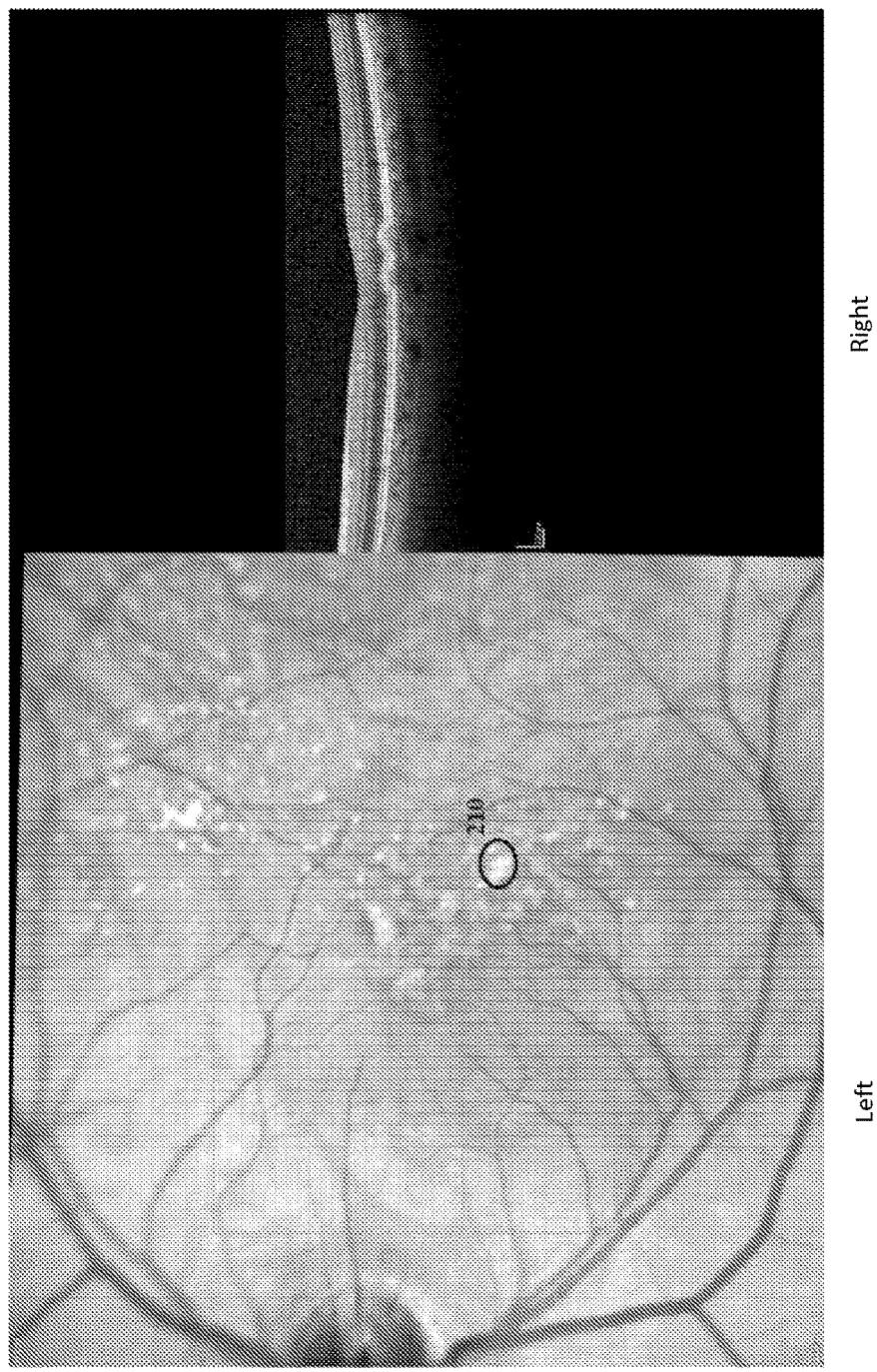
FIG. 2 depicts an image of the fundus of the eye (left) and corresponding OCT (right) of a patient with AMD.

FIG. 2 depicts an example of an OCT image and fundus image of the eye. The received data may comprise a plurality of sequential OCT and fundus images, and FIG. 2 depicts one of those slices. A possible druse 210 is also depicted at FIG. 2.

Referring again to FIG. 1B, the sequential OCT images received at 110 may be processed, at 120, to create a 3D model of the patient's retina. This model may include retina layers and metabolic consumption, concentration, or flux within or at the boundary of each layer. For example, the metabolic parameters may include one or more of the following: oxygen consumption at various locations/layers along the retina; oxygen influx at various locations/layers along the retina; oxygen diffusion at various locations/layers along the retina; steady state oxygen at various locations/layers along the retina; photoreceptor inner segments distances between 330 and 340 as described below, where most if not all of the metabolites/oxygen are consumed; metabolite flux/concentration at the interfaces with vasculature (for example, at 310 and 350); distance between metabolite source (310 and 350) and inner segments (region between 330 and 340). In some example implementations, the 3D patient-specific model may thus provide a three-dimensional representation of the patient's oxygen concentration at various layers of the eye.

In some implementations, a processor may segment the OCT images into one or more layers, such as 1 layer, 2 layers, 3 layers, 4 layers, and/or the like. This segmentation may be based on certain landmarks in the eye including the retina. For example, the processor may segment the image data from the patient using 6 intra-retinal boundaries which are as follows: Bruch's membrane; retinal pigment epithelium; Photoreceptor inner segment-outer segment junction; External limiting membrane; top of the outer nuclear layer; and top of the outer plexiform layer, although other types of segmentation may be performed as well.

Figure 3A:
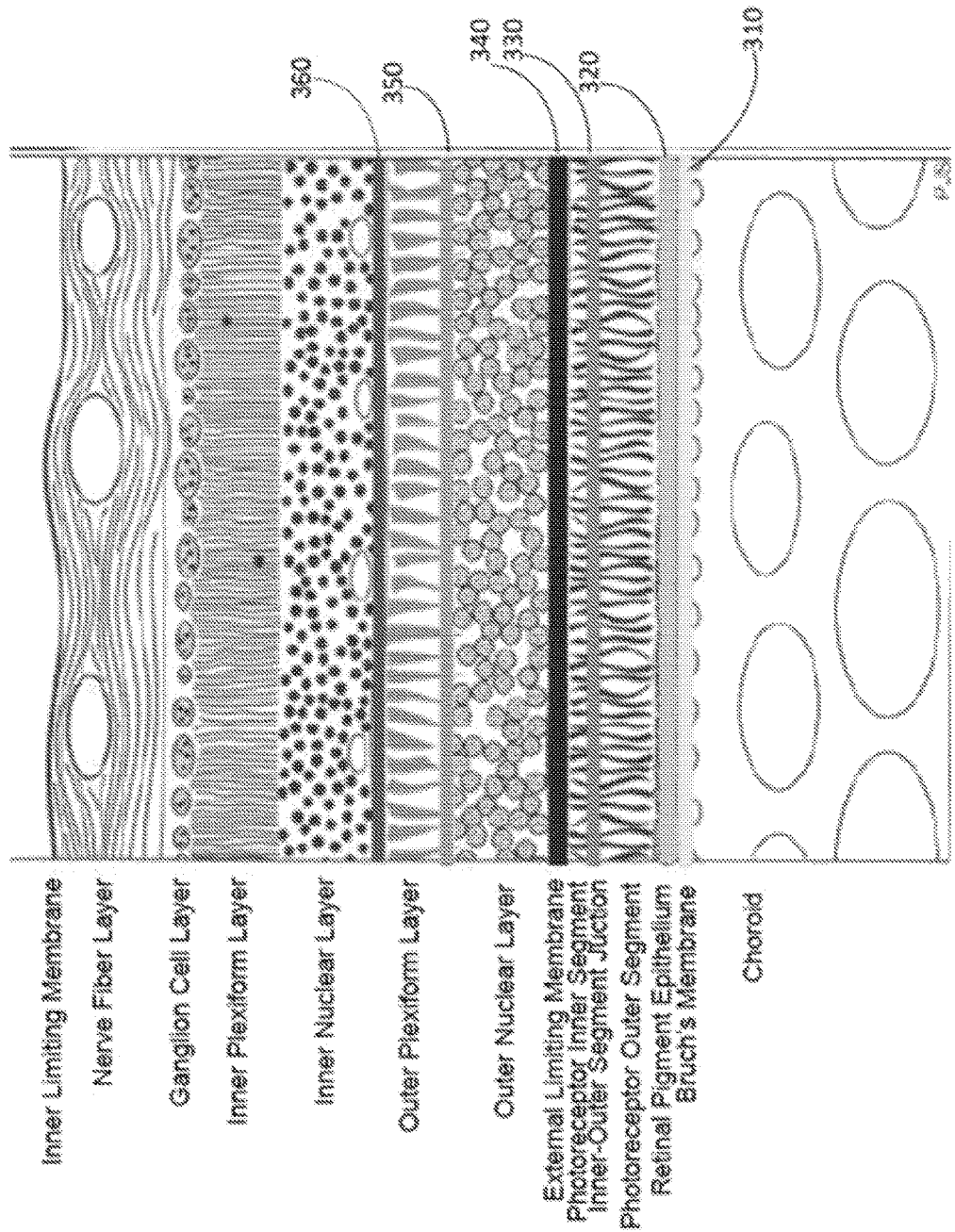
FIG. 3A depicts a schematic representation of retinal layers.
Figure 3B:
FIG. 3B depicts a visualization of the same layers using an OCT image of a patient with AMD.

FIG. 3A depicts a pictorial representation of the intra-retinal boundaries, and FIG. 3B depicts those boundaries in a single OCT image. The boundaries include Bruch's membrane 310; the retinal pigment epithelium 320; the photoreceptor inner segment-outer segment junction 330; the external limiting membrane 340; the top of the outer nuclear layer 350; and the top of the outer plexiform layer 360.

Figure 3C:
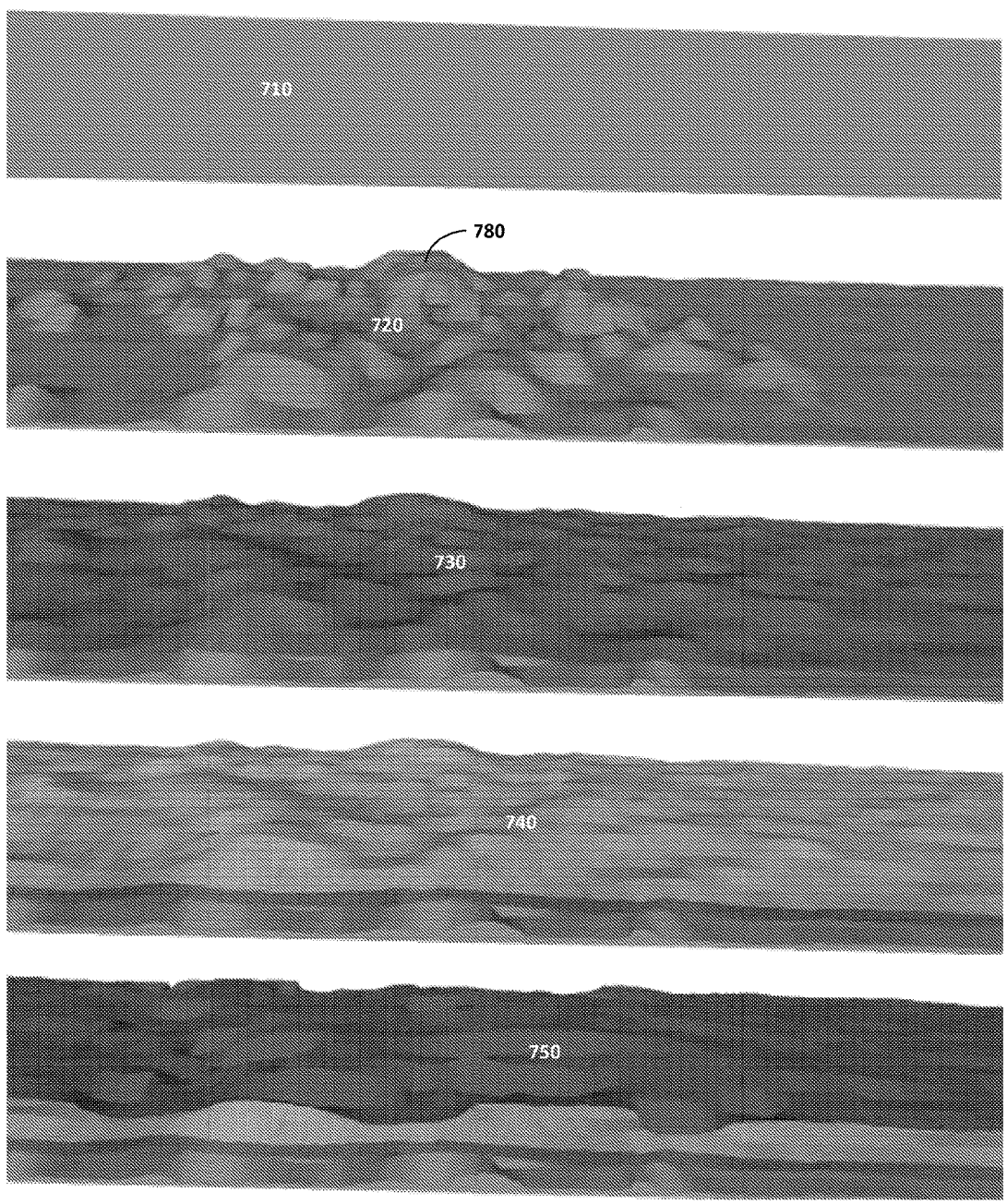
FIG. 3C depicts another visual representation of a portion of three-dimensional eye model including the morphology of the eye including retinal layer interfaces.
Figure 3D:
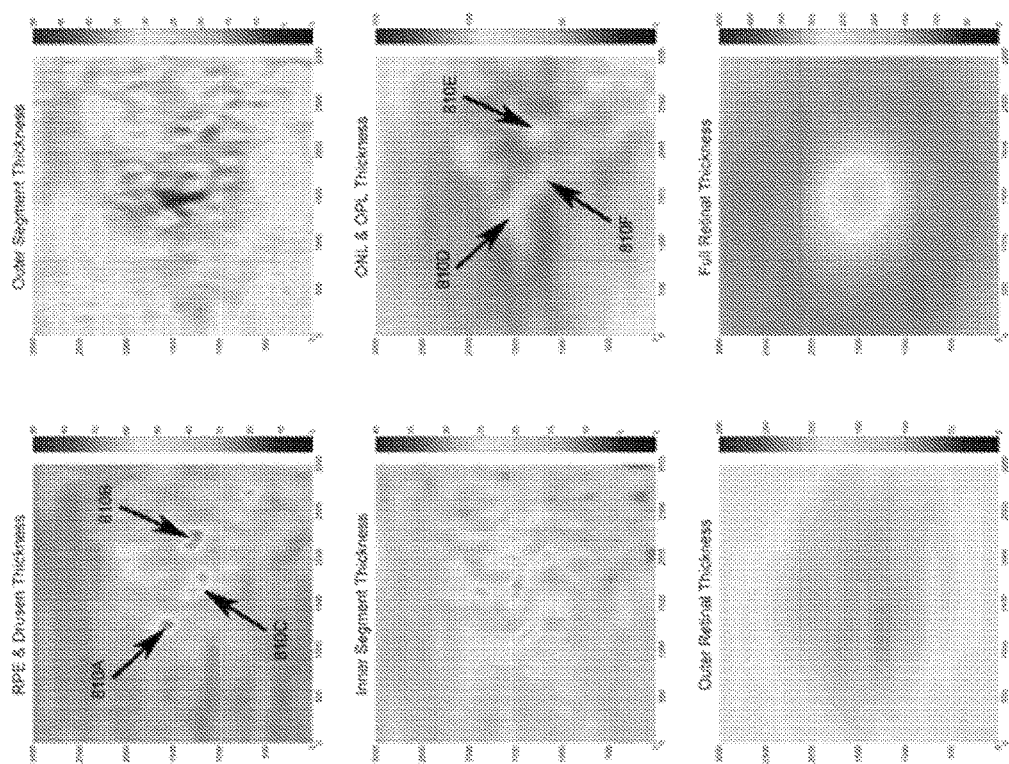
FIG. 3D depicts detected regions (at arrows) of outer nuclear layer thinning.

FIG. 3C depicts another visualization of a 3D patient-specific model including Bruch's membrane 710, the retinal pigment epithelium 720, the IS-OS junction 730, the external limiting membrane 740, and the top of the outer nuclear layer 750. A drusen also causes a deformation at 780 elevating the bottom of the retinal pigment epithelium 720. FIG. 3D shows a heat map of the retinal pigment epithelium (RPE) height and outer nuclear layer (ONL) thickness. The fovea where the ONL should be the thickest is located at approximately 2500-4000 microns on the x-axis and spans the full range of the y-axis. Regions of elevated RPE (which indicate drusen) may be co-located with ONL thinning as depicted by arrows 810A-F as detected by process 100.

Referring again to FIG. 1B at 120, in some example implementations, the received OCT and fundus images may be combined to form a 3D patient-specific model of the patient's retina including one or more parameters corresponding to the locations and/or layers of the retina. For example, the OCT images segmented into retinal layers as noted above may be further processed by computer 170 into a 3D patient-specific model to provide a so-called map of the patient's outer retina. Specifically, the processing may identify common landmarks based on relative pixel locations and known pixel-to-distance scales to combine multiple sequential OCT and fundus images. Moreover, computer 170 may further process (for example, using finite element analysis) the 3D patient-specific model of the patient's retina to determine or associate parameters, such as metabolite/oxygen concentration, with the layers/locations and to determine regions of interest, such as regions of hyperoxia and hypoxia in the retina. Specifically, finite element analysis may be used to determine for a given 3D patient-specific model and its morphology, the oxygen state (for example, steady state oxygen state) given a value of oxygen consumption, fixed oxygen concentration or influx at layer boundaries, oxygen partial pressure, oxygen diffusion through segmented layers of the retina, and/or other parameters.

Table 1 depicts example values that may be used by the finite element analysis tool to determine oxygen diffusion, oxygen consumption, oxygen influx, and oxygen concentration/partial pressure at various locations along the retina. For example, given a certain layer having a certain area, the oxygen diffusion may be estimated in that layer based on the value given in Table 1 below. Although the values below are for cats and monkeys, human data may be used as well.

TABLE 1

Initial modeling parameters

| Variable | Value | Species | Source |
| --- | --- | --- | --- |
| Oxygen diffusivity in retina | $1.97 \times 10^{-5}$ $cm^2$/sec | Cat | [Roh et al., 1990] |
| Oxygen consumption by inner segments | 3.33 µl/ (g * sec) | Cat | [Avtar & Tandon, 2008] |
| Amount of oxygen supplied by choroid | 85%/89% (in dark/light) | Monkey | [Linsenmeier & Padnick-Silver, 2000; Birol et al., 2007] |
| Partial pressure of oxygen at choroid | 48 mmHg | Monkey | [Birol et al., 2007] |
| Partial pressure of oxygen at inner segment | 3.8 mmHg | Monkey | [Birol et al., 2007] |

To illustrate further, computer 170 may input patient-specific morphological data of retinal layers into a finite element modeling tool (although another three-dimensional processing tool may be used as well). Given this geometry and a set of input parameters, computer 170 may, based on a finite element analysis, calculate steady-state oxygen concentration—identifying regions of hypoxia or hyperoxia at various locations and/or layers of the retina.

If the oxygen concentration at a given location is above or below predetermined thresholds, the computer 170 may detect, at 130, the given location as a region of interest, such as a hyperoxic region or hypoxic region, both of which represent a risk for diseases of the eye, such as AMD and/or the like. These regions may also correlate with drusen, and the process 100 may correlate the detected regions with the locations and shapes of drusen which may also be detected at 130 by the finite element modeling tool using the morphology of the retinal layers. This correlation may further enhance the detection a risk for a disease of the eye, such as AMD, and/or the like. The predetermined thresholds may be determined programmatically or provided by a user to identify hyperoxic region or hypoxic regions.

At 140, a comparison may also be made with a 3D reference model. For example, the detected regions of hyperoxia or hypoxia including their associated parameters, such as size of detected region, location of detected region, amount of metabolite or oxygen concentration/deficiency, and/or the like, may be compared to the 3D reference model. This comparison may provide an indication of the likelihood that the regions represent a disease of the retina, a speed of disease progression, and/or the like. For example, the 3D reference model may include reference data collected over time for a plurality of patients, so the comparison against the 3D reference model may be indicative of the likelihood that the regions represent a disease of the retina, a speed of disease progression, and/or the like.

In some example embodiments, the 3D reference model may be gathered using a process similar to process 100, but the reference model includes data from a plurality of patients, which may be collected over time. Indeed, after the analysis for a given patient is completed using processes 100, the patient's data may be anonymized and then included in the 3D reference model. Moreover, the 3D reference model may include data for the one or more patient having AMD or some other retina disease collected over time, in which case the 3D reference model may provide an indication of the likelihood that the patient (whose data is provided at 110 and then compared to the reference model at 140) will progress to AMD and the speed of the progression, although other data for other types of disease may be collected as well.

At 150, a processor, such as a computer 170, may provide the results of the comparison, and the results may include a prediction. In some example embodiments, the steady-state oxygen/metabolite concentrations calculated at 130 and the comparison to the reference model at 140 may provide predictions about future retinal degeneration, such as photoreceptor thinning (which is related to vision loss, in diseases such as AMD). These predictions may indicate the speed, degree, and location of retinal degeneration.

Although the previous example refers to oxygen as a metabolite which serves as an indicator of retina thinning and possible vision loss, other metabolites including for example glucose, vitamin A, and/or other metabolites may be used as well in process 100 to predict future retinal degeneration which is related to vision loss.

Moreover, although some of the previous examples refer to specific diseases of the eye, the 3D modeling of the retinal layers including metabolite/oxygen in 3D (for example, at various layers and at various locations) may be used with other diseases of the eye associated with photoreceptor thinning.

Figure 4A:
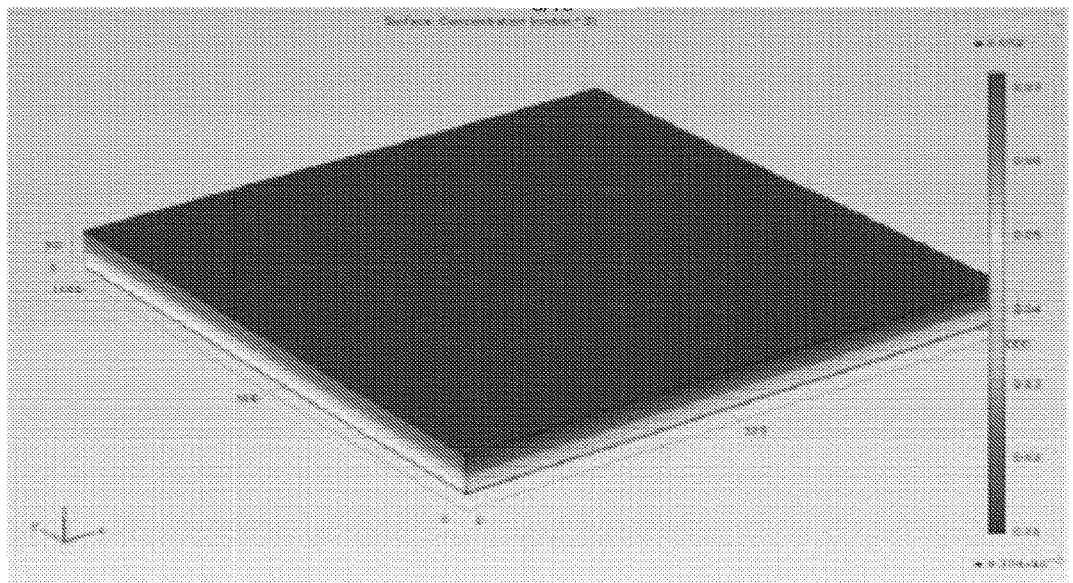
FIG. 4A depicts another visual representation of a portion of a three-dimensional eye model.
Figure 4A:
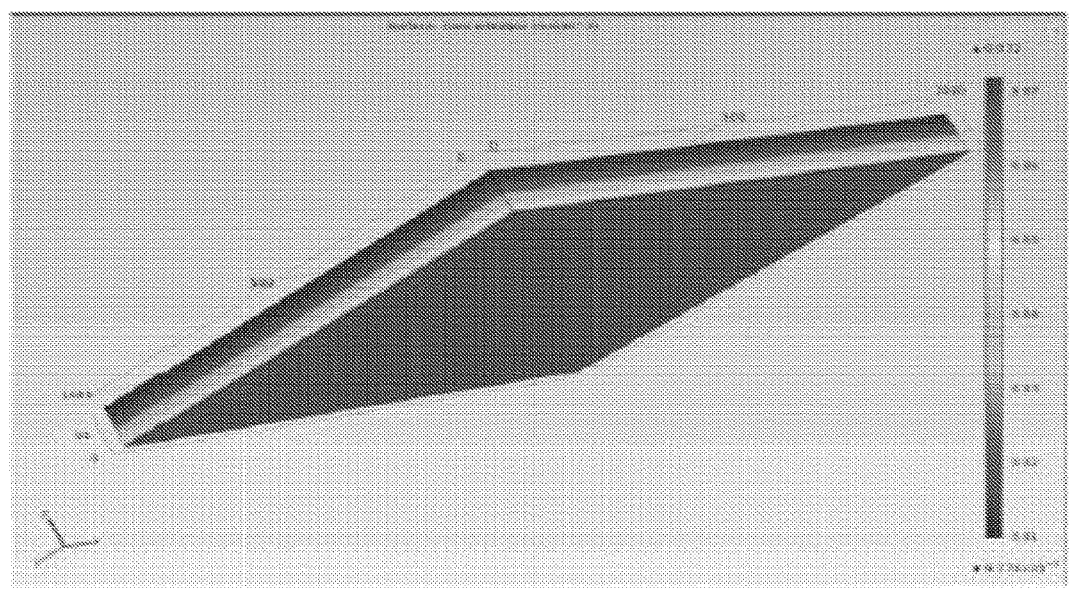
Figure 4B:
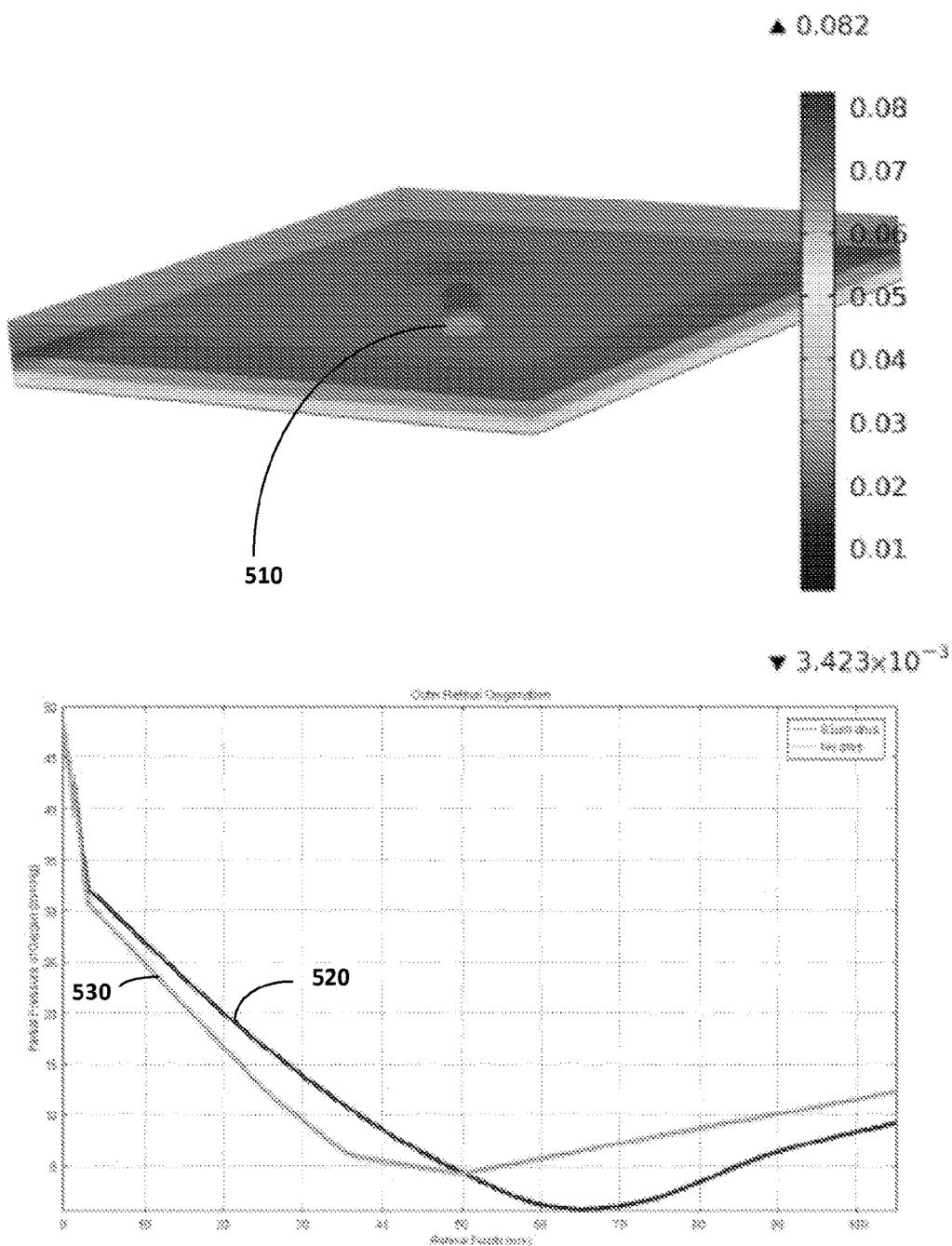
FIGS. 4B-4C depict visual representations of a portion of a three-dimensional eye model including a druse and oxygen concentration at the druse.
Figure 4C:
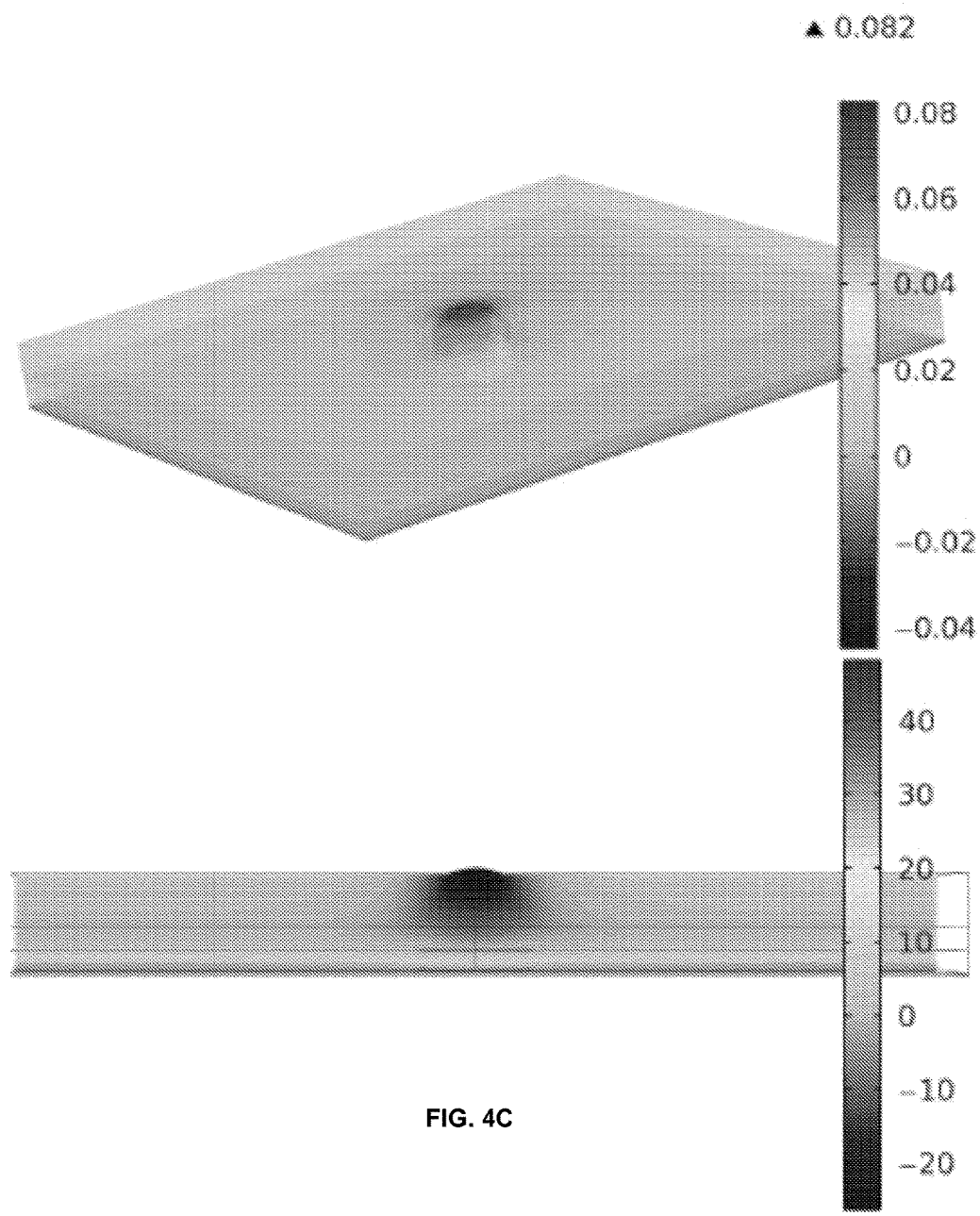

FIG. 4A depicts a plot of a generic example of a 3D model of an eye, and FIG. 4B depicts a generic example of a 3D model of an eye including a single druse 510. Also depicted at FIG. 4B is a plot 520 of the oxygen concentration through the depth of the retina passing through the center of the hemispherical druse 63 µm in diameter with the zero x-coordinate spatially representing the choriocapillaris-Bruch's membrane interface. Plot 530 depicts the oxygen concentration through a retina without any drusen. Note the decrease in minimum oxygen concentration in 520 compared to 530 suggesting a mildly hypoxic region of the retina. FIG. 4C also depicts another generic 3D model displaying oxygen concentration in the retina with a hemispherical druse having a diameter of 125 microns. In the example shown at FIG. 4C, the oxygen concentration goes below zero potentially indicating a critical level of hypoxia in which cells are not receiving sufficient oxygen to survive and function leading to retinal degeneration.

In the example of FIGS. 4B and 4C, drusen are shown having diameters of about 63 µm (FIG. 4B) and about 125

μm (FIG. 4C). Hemispherical drusen below a critical size may not induce complete oxygen depletion, while larger drusen may induce oxygen depletion. The 3D shape and distribution of drusen may be a factor in changes to retinal oxygenation. This may, in some implementations, be another benefit of the 3D modeling disclosed herein as only the lateral dimension are used to diagnose drusen size for AMD, rather than using height which has been speculated to be a more important factor—supporting the idea that increased diffusion distance may play a key role in some forms of retinal degeneration. For example, a druse small in the lateral dimension, but tall in height may be incorrectly identified as non-pathological using past approaches methods while the approach described herein may be able to detect the resulting pathological hypoxia and subsequent retinal degeneration.

Figure 5A:
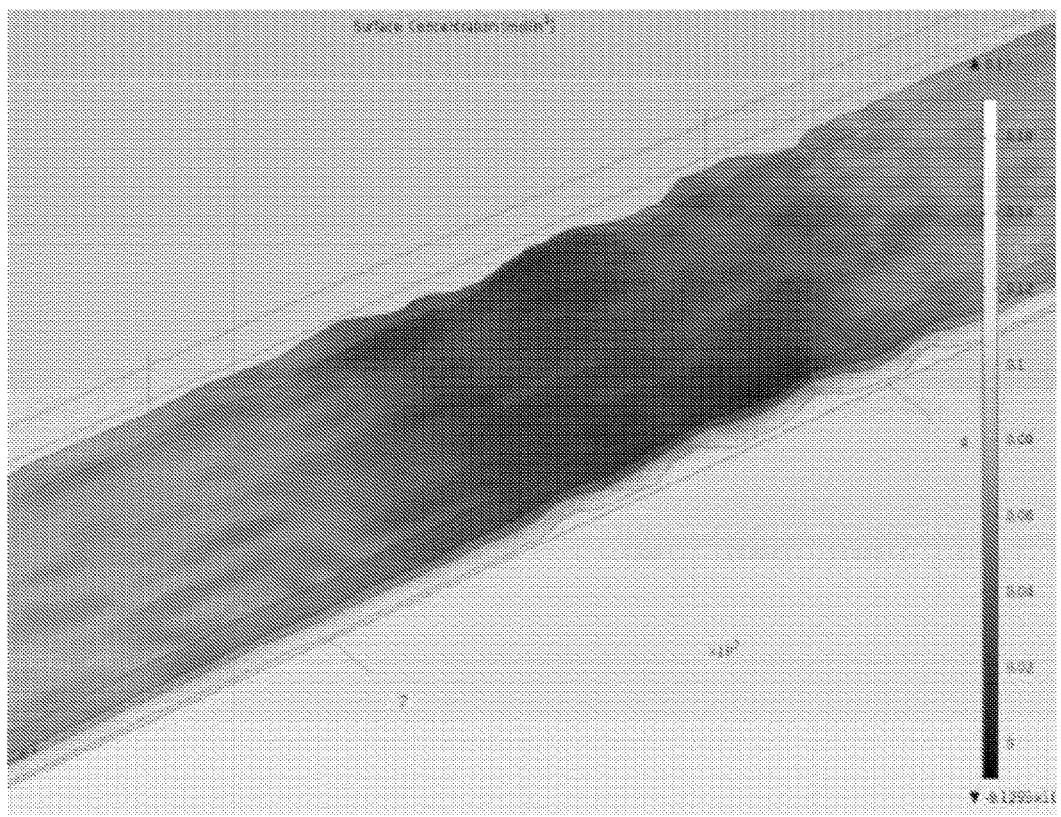
FIG. 5A depicts a visual representation of a portion of a patient-specific three-dimensional model eye including retinal layers created based on OCT images.
Figure 5B:
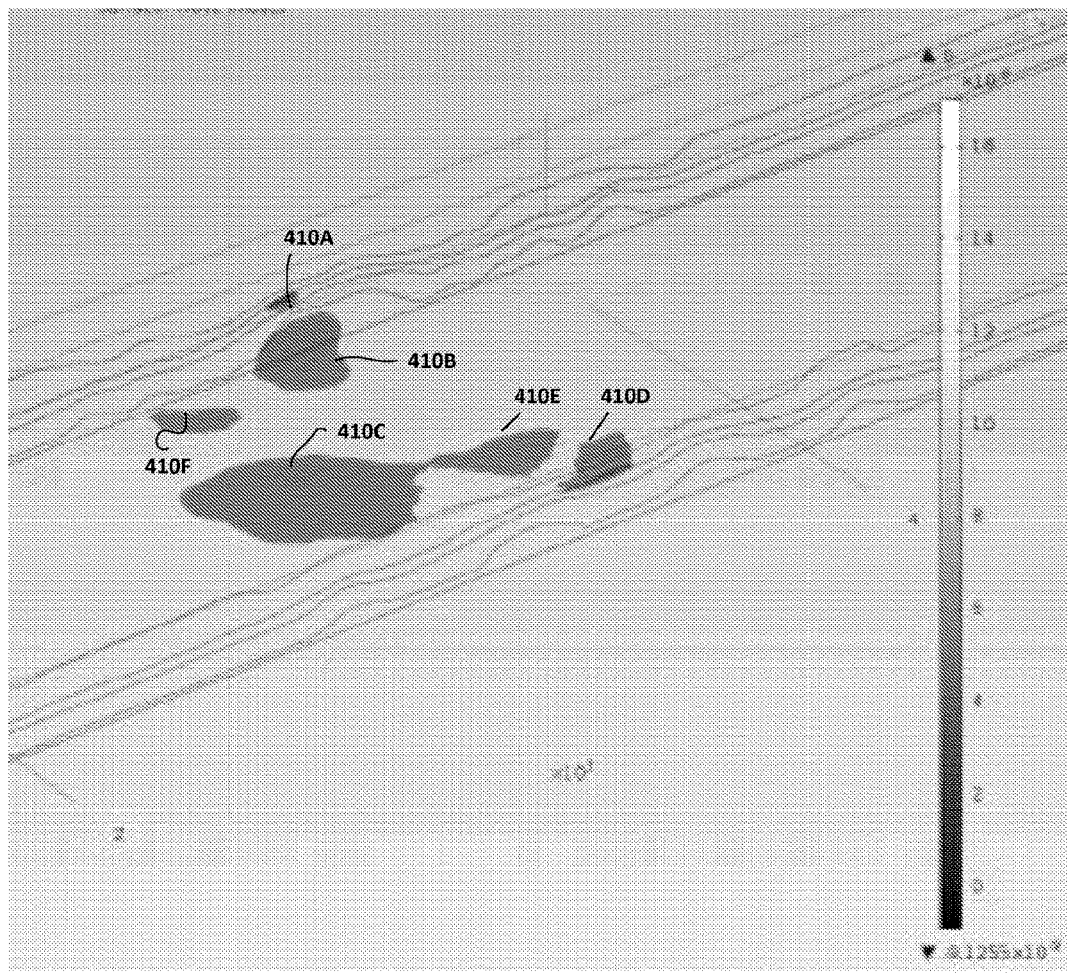
FIG. 5B depicts a visual representation of a portion of a three-dimensional eye model including retinal layers and detected regions of hypoxia.
Figure 5C:
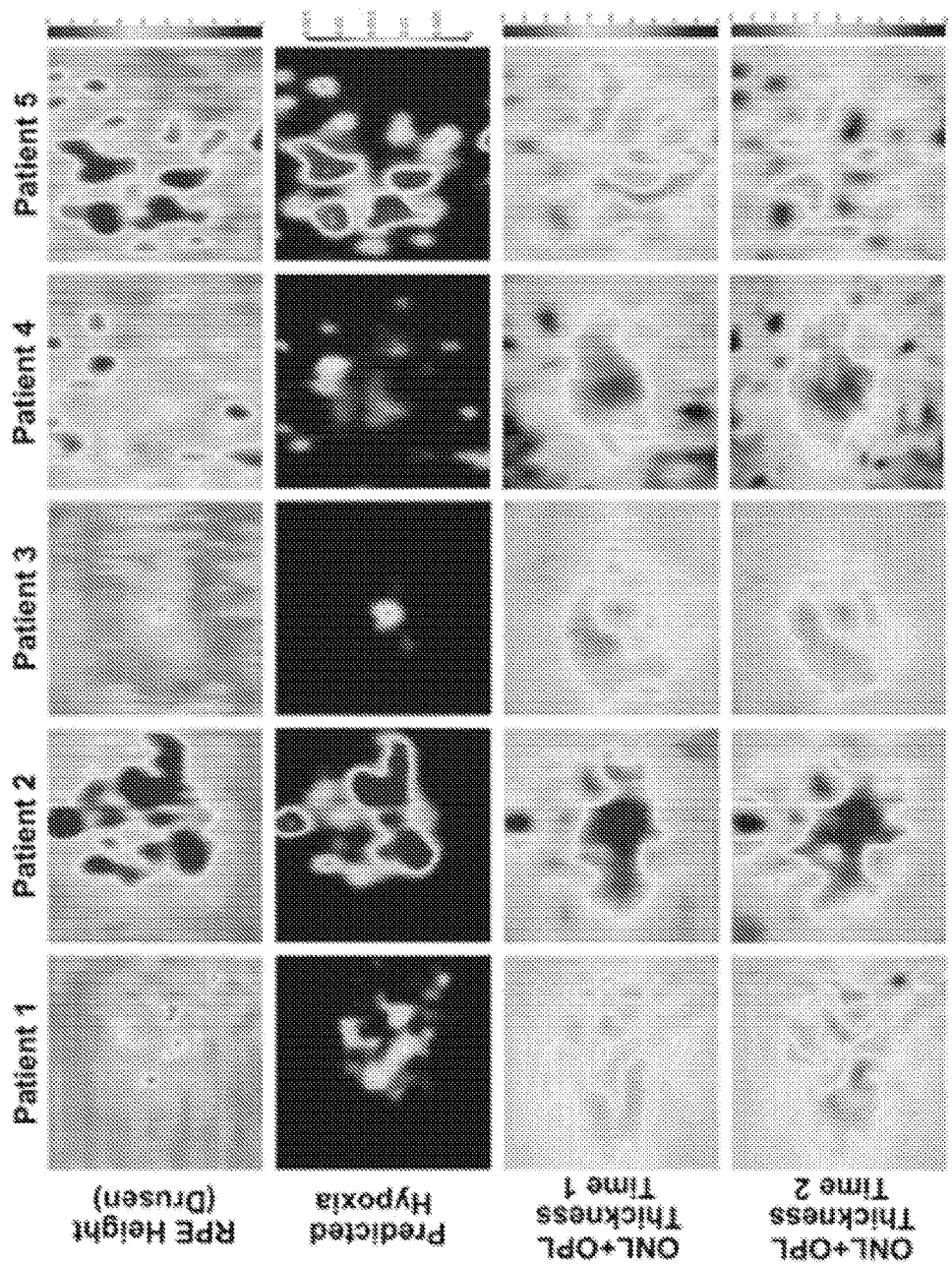
FIG. 5C depicts the regions of predicted hypoxia versus change in photoreceptors (ONL+OPL) thickness for five individual patients.

FIG. 5A depicts an example morphology of the eye processed using the above-noted finite element analysis to determine oxygen concentration throughout the retina. FIG. 5B depicts hypoxic regions detected at 130 (see, e.g., 410A-F at FIG. 5B). FIG. 5C depicts the area of predicted hypoxia for five individual patients versus changes in photoreceptor thickness shown by the ONL+OLP thickness between time 1 and time 2. Each column represents an individual patient. The first row depicts RPE height which is corollary for drusen height as RPE height variance is negligible. Row 2 depicts the regions predicted to be hypoxic based on computational modeling of retinal geometry collected at Time 1. Row 4 and 5 are the thickness of ONL and OPL combined at Time 1 and Time 2 respectively. Rows 1, 3, and 4 color bars are height in μm, row 2 is oxygen concentration in millimolar.

In some implementations, the ability of process 100 to predict vision loss may depend in part on the 3D reference model, which may also be referred to as training data and/or historical data. The 3D reference model may include for example data collected from a plurality of diseased patients with existing OCT data from multiple exams over the course of years. By comparing these different time points, the reference model can be trained to associate changes in oxygen concentration with future retinal degeneration. However, though retinal thinning is widely thought to result in reduced vision, the 3D reference model may be most beneficial if this reduction can be quantified. Therefore, microperimetry may be used to correlate vision loss at a particular location to outer nuclear layer thickness using OCT data. Due to the precision of this approach, a specific pathological entity, such as a druse in AMD, may be correlated to future retinal thinning and associated vision loss at a particular area within the visual field.

Although ordinal numbers such as first, second, and/or the like, can, in some situations, relate to an order; as used in this document ordinal numbers do not necessarily imply an order. For example, ordinal numbers can be merely used to distinguish one item from another. For example, to distinguish a first event from a second event, but need not imply any chronological ordering or a fixed reference system (such that a first event in one paragraph of the description can be different from a first event in another paragraph of the description).

The foregoing description is intended to illustrate but not to limit the scope of the invention, which is defined by the scope of the appended claims. Other implementations are within the scope of the following claims.

The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above. Other implementations can be within the scope of the following claims.

What is claimed:

1. A method of predicting retinal degeneration, the method comprising:
   receiving three-dimensional data representative of a plurality of layers of a retina of a subject under test;
   generating, based on the received three-dimensional data, a three-dimensional model specific to the subject under test, the three-dimensional model characterizing a three-dimensional shape of at least one of the plurality of layers of the retina, the shape including a thickness that varies over the at least one of the plurality of layers;
   determining, from the generated three-dimensional model, oxygen concentration at one or more of the plurality of layers;
   detecting, based on the determined oxygen concentration, a region of at least one a high oxygen concentration in the retina and/or a low oxygen concentration in the retina; and
   comparing the detected region to a three-dimensional reference model to determine that the retina including the detected region suffers from or will suffer from at least one of a retinal disease or a degeneration of the retina, wherein the receiving, the determining, the generating, the detecting, and the comparing are performed by at least one processor forming part of at least one computing system.

2. The method of claim 1, wherein the three-dimensional data comprises an optical coherence tomography image of the subject under test and/or a fundus image of the subject under test.

3. The method of claim 1, wherein the determining further comprises:
   determining the oxygen concentration at, or between, one or more of the at least one of the plurality of layers, wherein the plurality of layers includes a Bruch's membrane; a retinal pigment epithelium; a photoreceptor inner segment-outer segment junction; an external limiting membrane; a top of the outer nuclear layer; and a top of the outer plexiform layer.

4. The method of claim 1, wherein the three-dimensional reference model includes oxygen concentration data obtained from one or more patients having the at least one of the retinal disease or the degeneration of the retina.

5. The method of claim 1, wherein the at least one of the retinal disease or the degeneration of the retina comprises at least one of a retinal thinning; an age-related macular degeneration (AMD) or progression thereof; a retinal edema; retinal detachment; photo-receptor thinning; or a central serous retinopathy.

6. The method of claim 1, wherein the detecting further comprises:
   comparing the detected region to a high oxygen concentration threshold in the retina or a low oxygen concentration threshold in the retina.

7. A system for predicting retinal degeneration, the system comprising:
   at least one processor; and
   at least one memory including code, which when executed by the at least one processor provides operations comprising:
   receiving three-dimensional data representative of a plurality of layers of a retina of a subject under test;
   generating, based on the received three-dimensional data, a three-dimensional model specific to the subject under test, the three-dimensional model characterizing a three-dimensional shape of at least one of the plurality of layers of the retina, the shape including a thickness that varies over the at least one of the plurality of layers;
   determining, from the generated three-dimensional model, oxygen concentration at one or more of the plurality of layers;
   detecting, based on the determined oxygen concentration, a region of at least one a high oxygen concentration in the retina and/or a low oxygen concentration in the retina; and
   comparing the detected region to a three-dimensional reference model to determine that the retina including the detected region suffers from or will suffer from at least one of a retinal disease or a degeneration of the retina.

8. The system of claim 7, wherein the three-dimensional data comprises an optical coherence tomography image of the subject under test and/or a fundus image of the subject under test.

9. The system of claim 7, wherein the determining further comprises:
   determining the oxygen concentration at, or between, one or more of the at least one of the plurality of layers, wherein the plurality of layers includes a Bruch's membrane; a retinal pigment epithelium; a photoreceptor inner segment-outer segment junction; an external limiting membrane; a top of the outer nuclear layer; and a top of the outer plexiform layer.

10. The system of claim 7, wherein the three-dimensional reference model includes oxygen concentration data obtained from one or more patients having the at least one of the retinal disease or the degeneration of the retina.

11. The system of claim 7, wherein the at least one of the retinal disease or the degeneration of the retina comprises at least one of a retinal thinning; an age-related macular degeneration (AMD) or progression thereof; a retinal edema; retinal detachment; photo-receptor thinning; or a central serous retinopathy.

12. The system of claim 7, wherein the detecting further comprises:
   comparing the detected region to a high oxygen concentration threshold in the retina or a low oxygen concentration threshold in the retina.

13. The system of claim 7, wherein the three-dimensional model includes a parameter associated with the at least one of the plurality of layers, the parameter characterizing steady state oxygen state, oxygen consumption, fixed oxygen concentration, influx at layer boundary, oxygen partial pressure, and/or oxygen diffusion.

14. The system of claim 7, wherein the at least one of the plurality of layers corresponds to one or more of the following layers: a Bruch's membrane; a retinal pigment epithelium; a photoreceptor inner segment-outer segment junction; an external limiting membrane; a top of the outer nuclear layer; and a top of the outer plexiform layer.

15. The system of claim 14, further comprising:
   segmenting the three: dimensional data into the plurality of layers;
   wherein the three-dimensional model characterizes the three-dimensional shape of:
   a first layer corresponding to the Bruch's Membrane;
   a second layer corresponding to the retinal pigment epithelium;
   a third layer corresponding to the photoreceptor inner segment-outer segment junction;
   a fourth layer corresponding to the external limiting membrane;
   a fifth layer corresponding to the top of the outer nuclear layer; and
   a sixth layer corresponding to the top of the outer plexiform layer.

16. The system of claim 15, wherein the three-dimensional model further includes:
   a first parameter associated with the first layer, the first parameter characterizing steady state oxygen state, oxygen consumption, fixed oxygen concentration, influx at layer boundary, oxygen partial pressure, and/or oxygen diffusion;
   a second parameter associated with the second layer, the second parameter characterizing steady state oxygen state, oxygen consumption, fixed oxygen concentration, influx at layer boundary, oxygen partial pressure, and/or oxygen diffusion;
   a third parameter associated with the third layer, the third parameter characterizing steady state oxygen state, oxygen consumption, fixed oxygen concentration, influx at layer boundary, oxygen partial pressure, and/or oxygen diffusion;
   a fourth parameter associated with the fourth layer, the fourth parameter characterizing steady state oxygen state, oxygen consumption, fixed oxygen concentration, influx at layer boundary, oxygen partial pressure, and/or oxygen diffusion;
   a fifth parameter associated with the fifth layer, the fifth parameter characterizing steady state oxygen state, oxygen consumption, fixed oxygen concentration, influx at layer boundary, oxygen partial pressure, and/or oxygen diffusion; and
   a sixth parameter associated with the sixth layer, the sixth parameter characterizing steady state oxygen state, oxygen consumption, fixed oxygen concentration, influx at layer boundary, oxygen partial pressure, and/or oxygen diffusion.

17. A non-transitory computer-readable medium including computer code, which when executed by at least one processor provides operations for predicting retinal degeneration, the operations comprising:
   receiving three-dimensional data representative of a plurality of layers of a retina of a subject under test;
   generating, based on the received three-dimensional data, a three-dimensional model specific to the subject under test, the three-dimensional model characterizing a three-dimensional shape of at least one of the plurality of layers of the retina, the shape including a thickness that varies over the at least one of the plurality of layers;
   determining, from the generated three-dimensional model, oxygen concentration at one or more of the plurality of layers;

detecting, based on the determined oxygen concentration, a region of at least one a high oxygen concentration in the retina and/or a low oxygen concentration in the retina; and comparing the detected region to a three-dimensional reference model to determine that the retina including the detected region suffers from or will suffer from at least one of a retinal disease or a degeneration of the retina.

18. The non-transitory computer-readable medium of claim 17, wherein the three-dimensional data comprises an optical coherence tomography image of the subject under test and/or a fundus image of the subject under test.

19. The non-transitory computer-readable medium of claim 17, wherein the determining further comprises:

determining the oxygen concentration at, or between, one or more of the at least one of the plurality of layers, wherein the plurality of layers includes a Bruch's membrane; a retinal pigment epithelium; a photoreceptor inner segment-outer segment junction; an external limiting membrane; a top of the outer nuclear layer; and a top of the outer plexiform layer.

20. The non-transitory computer-readable medium of claim 17, wherein the three-dimensional reference model includes oxygen concentration data obtained from one or more patients having the at least one of the retinal disease or the degeneration of the retina.

21. The non-transitory computer-readable medium of claim 17, wherein the at least one of the retinal disease or the degeneration of the retina comprises at least one of a retinal thinning; an age-related macular degeneration (AMD) or progression thereof; a retinal edema; retinal detachment; photo-receptor thinning; or a central serous retinopathy.

* * * * *